(12) United States Patent
Jackson et al.

(10) Patent No.: US 6,605,552 B2
(45) Date of Patent: Aug. 12, 2003

(54) SUPERABSORBENT COMPOSITES WITH STRETCH

(75) Inventors: David Martin Jackson, Roswell, GA (US); Oomman Painummoottil Thomas, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/728,243

(22) Filed: Dec. 1, 2000

(65) Prior Publication Data

US 2002/0068494 A1 Jun. 6, 2002

(51) Int. Cl.$^7$ .................. D02G 3/00; B32B 27/38; B32B 5/16; C08G 18/08; C08G 18/10; C08F 2/46

(52) U.S. Cl. ............... 442/329; 442/414; 442/327; 442/328; 442/329; 442/333; 442/400; 442/401; 528/49; 528/75; 522/90

(58) Field of Search ............... 442/327–329, 442/333, 400–401, 414

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann et al. | |
| 3,542,615 A | 11/1970 | Dobo et al. | |
| 3,692,618 A | 9/1972 | Dorschner et al. | |
| 3,802,817 A | 4/1974 | Matsuki et al. | 425/66 |
| 3,849,241 A | 11/1974 | Butin et al. | 161/169 |
| 4,041,203 A | 8/1977 | Brock et al. | |
| 4,100,324 A | 7/1978 | Anderson et al. | 428/288 |
| 4,318,408 A * | 3/1982 | Korpman | 128/287 |
| 4,340,563 A | 7/1982 | Appel et al. | |
| 4,356,288 A * | 10/1982 | Lewis et al. | 525/308 |
| 4,426,417 A | 1/1984 | Meitner et al. | 428/195 |
| 4,429,001 A | 1/1984 | Kolpin et al. | 428/283 |
| 4,449,977 A | 5/1984 | Korpman | 604/366 |
| 4,469,734 A | 9/1984 | Minto et al. | 428/134 |
| 4,604,313 A | 8/1986 | McFarland et al. | 428/172 |
| 4,640,810 A | 2/1987 | Laursen et al. | 264/518 |
| 4,652,487 A | 3/1987 | Morman | |
| 4,655,757 A | 4/1987 | McFarland et al. | 604/366 |
| 4,655,760 A | 4/1987 | Morman et al. | |
| 4,657,802 A | 4/1987 | Morman | |
| 4,707,398 A | 11/1987 | Boggs | 428/224 |
| 4,720,415 A | 1/1988 | Vander Wielen et al. | |

(List continued on next page.)

FOREIGN PATENT DOCUMENTS

| | | | |
|---|---|---|---|
| DE | 3905761 | 8/1990 | |
| EP | 0 272 682 | 6/1988 | |
| EP | 0 309 187 | 3/1989 | |
| EP | 0559911 | 9/1993 | |
| EP | 0773315 | 5/1997 | |
| EP | 0 990 726 | 4/2000 | D04B/21/04 |
| EP | 0 992 250 | 4/2000 | A61L/15/60 |
| WO | 91/01766 | 2/1991 | A61L/15/24 |
| WO | 97/23181 | 7/1997 | A61F/13/15 |
| WO | 99/05346 | 2/1999 | D01F/6/80 |
| WO | 99/34041 | 7/1999 | D01F/6/36 |

OTHER PUBLICATIONS

Dow Corning Corporation, "Guide to the Fluid Resistance of SILASTIC® Silicone Rubber", © 1984 Dow Corning Corporation, pp. 1–5 and 27–36.

DuPont, Design Guide—Module V, "Hytrel® engineering thermoplastic elastomer", Jan. 1995, cover page and back cover plus pp. 6–9.

(List continued on next page.)

*Primary Examiner*—Terrel Morris
*Assistant Examiner*—Lynda Salvatore
(74) *Attorney, Agent, or Firm*—Steven D. Flack

(57) ABSTRACT

There is provided layer for personal care products made from elastic polymers that are extruded and cross-linked to form superabsorbents. Such a layer is useful in personal care products, like diapers, training pants, incontinence garments and feminine hygiene products.

14 Claims, 2 Drawing Sheets

U.S. PATENT DOCUMENTS

| | | | |
|---|---|---|---|
| 4,724,114 A | 2/1988 | McFarland et al. | 264/510 |
| 4,741,949 A | 5/1988 | Morman et al. | 428/224 |
| 4,767,825 A | 8/1988 | Pazos et al. | 525/408 |
| 4,781,966 A | 11/1988 | Taylor | |
| 4,789,699 A | 12/1988 | Kieffer et al. | |
| 4,803,117 A * | 2/1989 | Daponte | 428/228 |
| 4,806,598 A | 2/1989 | Morman | 525/63 |
| 4,818,464 A | 4/1989 | Lau | 264/510 |
| 4,820,577 A | 4/1989 | Morman et al. | 428/228 |
| 4,828,911 A | 5/1989 | Morman | 428/288 |
| 4,847,141 A | 7/1989 | Pazos et al. | 428/226 |
| 4,855,179 A | 8/1989 | Bourland et al. | 428/296 |
| 4,880,868 A | 11/1989 | Le-Khac | 524/549 |
| 4,902,463 A | 2/1990 | Tanaka et al. | 264/122 |
| 4,902,559 A | 2/1990 | Eschwey et al. | 428/224 |
| 4,931,005 A | 6/1990 | Tanaka et al. | 425/83.1 |
| 4,963,638 A | 10/1990 | Pazos et al. | 528/65 |
| 4,965,122 A | 10/1990 | Morman | |
| 4,981,747 A | 1/1991 | Morman | |
| 5,047,456 A | 9/1991 | Onwumere et al. | 524/13 |
| 5,066,742 A | 11/1991 | Gupta | 526/216 |
| 5,145,727 A | 9/1992 | Potts et al. | |
| 5,169,706 A | 12/1992 | Collier, IV et al. | |
| 5,178,931 A | 1/1993 | Perkins et al. | |
| 5,188,885 A | 2/1993 | Timmons et al. | |
| 5,204,110 A | 4/1993 | Cartmell et al. | |
| 5,219,974 A | 6/1993 | Onwumere et al. | |
| 5,226,992 A | 7/1993 | Morman | |
| 5,277,976 A | 1/1994 | Hogle et al. | 428/397 |
| 5,324,561 A | 6/1994 | Rezai et al. | |
| 5,336,545 A | 8/1994 | Morman | |
| 5,338,766 A | 8/1994 | Van Phan et al. | 521/63 |
| 5,366,452 A | 11/1994 | Widlund et al. | 604/385.2 |
| 5,451,219 A | 9/1995 | Suzuki et al. | 604/385.2 |
| 5,491,210 A | 2/1996 | Onwumere et al. | |
| 5,506,035 A | 4/1996 | Van Phan et al. | 428/196 |
| 5,560,878 A | 10/1996 | Dragoo et al. | 264/115 |
| 5,601,542 A | 2/1997 | Melius et al. | 604/368 |
| 5,645,542 A | 7/1997 | Anjur et al. | 604/368 |
| 5,662,634 A | 9/1997 | Yamamoto et al. | 604/378 |
| 5,683,374 A | 11/1997 | Yamamoto et al. | 604/385.2 |
| 5,817,391 A | 10/1998 | Rock et al. | 428/8.6 |
| 5,912,302 A * | 6/1999 | Gadkari et al. | 525/127 |
| 5,997,791 A | 12/1999 | Chou et al. | 264/210.8 |
| 6,133,173 A * | 10/2000 | Riedel et al. | 442/400 |

OTHER PUBLICATIONS

Elf Atochem, Pebax®—Basis of Performance "Breathable Films—Polyether Block Amides", Apr. 1996, with Pebax® Technical Information inserts dating from May 1994 (6 insert pages).

Elf Atochem, Pebax®—Basis of Performance "Polyether Block Amides", May 1997, pp. 1, 3–4.

Ikeda, Y. et al., "Polyurethane elastomer with PEO–PTMO–PEO soft segment for sustained release of drugs", *Biomaterials*, 1990, vol. 11, Oct., pp. 553–560.

Kimberly–Clark Corporation, "Hygiene—Elastomeric absorbent structure", *Medical Textiles*, Apr. 1998, pp. 4–6.

Lambda, N.M.K. et al., *"Polyurethanes in Biomedical Applications"*, 1998, CRC Press, pp. 13–14.

* cited by examiner $CH_2=CH-C(O)-O-(CH_2CH_2-O)_4-C(O)-CH=CH_2$

PEGDA

NVP

SUPERABSORBENT COMPOSITES WITH STRETCH

BACKGROUND OF THE INVENTION

The present invention concerns nonwoven materials mainly for use in personal care products like diapers, training pants, swim wear, absorbent underpants, adult incontinence products and feminine hygiene products. This material may also be used other applications such as, for example, in bandages and wound dressings, nursing pads and in veterinary and mortuary applications.

Personal care articles usually have multiple layers of material of some sort to absorb liquids from the body. These layers may include natural fibers, synthetic fibers and superabsorbent particles in varying proportions. When liquid such as urine is deposited into a personal care product like a diaper, it goes through the uppermost layers, typically a liner positioned against the body and a "surge" layer designed to provide temporary liquid hold-up. The product may also have a "distribution" layer designed to move liquid in the X and Y directions in order to utilize more of the absorbent core. After going through these upper layers, the urine enters the absorbent core portion of the product. The absorbent core permanently retains the liquid. Absorbent cores are typically composed of superabsorbent particles or mixtures of superabsorbent particles and pulp.

The conformability and comfort of the personal care product is an important matter for wearers. Personal care products should be able to move with the wearer without falling off or becoming entangled. They should not stretch (without recovery) to the point where waste material may escape from the diaper. Past materials for personal care products have included superabsorbents, generally as particles. These particles may move relatively independently as a garment is stretched and so do not impede the wearer's movement. They also require containment of some sort to prevent them from falling out of the product or coming in contact with the wearer's skin. While superabsorbent particles do not significantly reduce the elasticity of a personal care product, neither do they contribute to it. As a result, other components of the personal care product must provide the necessary elasticity. The end result is a personal care product that is no doubt bulkier than it could be if the superabsorbent also contributed in some way to the elasticity of the product.

It would be very desirable to have one material having absorbency and elastic properties so that personal care products may be made less bulky and more simple to construct. Such a material would also avoid the undesirable feature of superabsorbent particle leakage from the product since it would not be in particulate form. There remains a need, therefore, for a superabsorbent that will have good elastic properties and provide absorbent properties in the recesses of the body.

SUMMARY OF THE INVENTION

In response to the discussed difficulties and problems encountered in the prior art, a new material for use in personal care products has been discovered, where the material is made from an elastic acrylate-containing polymer which is extruded and is dimensionally stable and superabsorbent. The elastic polymer maybe extruded as a fiber, film, foam, fibrous film or fibrous foam. The extruded polymer may be mixed with pulp and/or synthetic fibers, particles (and mixtures thereof) to produce a layer having various predetermined amounts of superabsorbent and other fibers. One way of making the polymer for use in this inventions is by reacting an amine or hydroxy terminated polyether polyol with water and an isocyanate like isophorone di-isocyanate or toluene di-isocyanate.

The polymer layer may be stabilized by cross-linking it with a high energy beam such as an electron beam or an ultra-violet beam.

The layer of this invention is useful in personal care products like diapers, training pants, incontinence products, bandages, sanitary napkins and the like.

BRIEF DESCRIPTION OF THE DRAWINGS

A typical urethane synthetic scheme is given in FIG. 1. The formulas for a polyethylene glycol and N-vinyl pyrollidone are given in FIGS. 2 and 3 respectively.

Definitions

Figure 1:
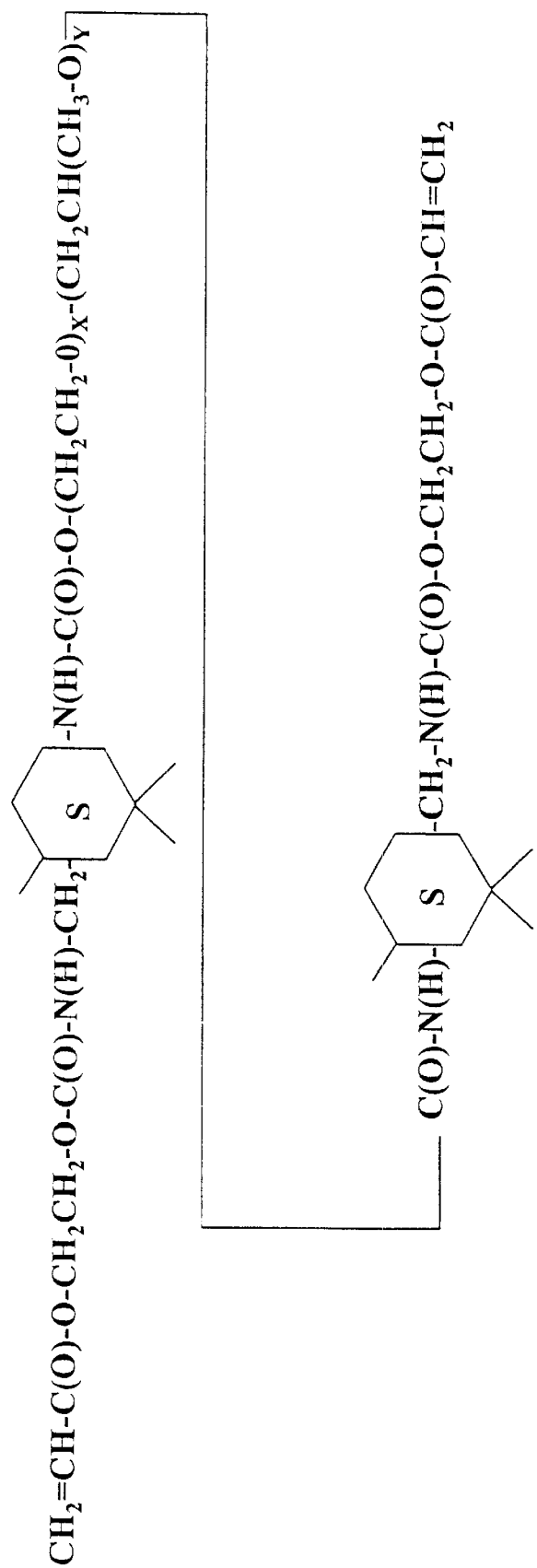

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 3,802,817 to Matsuki et al. The fibers may also have shapes such as those described, for example, in U.S. Pat. No. 5,277,976 to Hogle et al. which describes fibers with unconventional shapes.

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

As used herein, the term "coform" means a process in which at least one meltblown diehead is arranged near a chute through which other materials are added to the web while it is forming. Such other materials may be pulps, superabsorbent particles, natural polymers (for example, rayon or cotton fibers) and/or synthetic polymers (for example, polypropylene or polyester) fibers, for example, where the fibers may be of staple length. Coform processes are shown in commonly assigned U.S. Pat. Nos. 4,818,464 to Lau and 4,100,324 to Anderson et al. Webs produced by the coform process are generally referred to as coform materials.

"Airlaying" is a well-known process by which a fibrous nonwoven layer can be formed. In the airlaying process, bundles of small fibers having typical lengths ranging from about 3 to about 52 millimeters (mm), particularly around 12 mm, are separated and entrained in an air supply and then deposited onto a forming screen, usually with the assistance of an underlying vacuum supply. The randomly deposited fibers then are bonded to one another using, for example, hot air or a spray adhesive. Airlaying is taught in, for example, U.S. Pat. No. 4,640,810 to Laursen et al.

A "superabsorbent" is a material which is capable of absorbing a liquid under an applied load (AUL) in an amount of at least 15 g/g. The AUL value is expressed as the amount, in milliliters, of an aqueous 0.9 weight percent sodium chloride solution that the superabsorbent material can absorb per gram of superabsorbent material, in five minutes under a load of 2.0 kilopascals (approximately 0.3 pounds per square inch) while restrained from swelling in the plane normal to the applied load.

"Personal care product" means diapers, training pants, swim wear, absorbent underpants, adult incontinence products, bandages and feminine hygiene products. It may further encompass veterinary and mortuary products.

DETAILED DESCRIPTION OF THE INVENTION

This invention relates to a layer used in a personal care product to provide improved stretch in a layer incorporating superabsorbent.

The polymers provided herein may be cross-linked after processing, or may, depending on the formulation, cross-link as they are produced. Cross-linking the polymer of this invention provides needed dimensional stability. Conventionally available fibers produce rigid, glassy fibers. Fibers made from polymers of this invention are generally not rigid, or can be initially rigid and made less rigid through triggerable elasticity.

The layer of this invention may be made using a di- or multi-functional hydroxy or amine terminated polyether or polyester polyol, coupled through isocyanates in a one or two step process with chain extension, to create phase segregation in the polymer. The polyol may be polyethylene oxide which may be co-polymerized with additional oxide monomers to provide frustrated chain packing, thereby creating lower crystalinity and increased elasticity.

One way of making the polymer of this invention is to use a difunctional isocyanate such as isophorone di-isocyanate (IPDI) or toluene di-isocyanate (TDI) reacted with a hydroxy functionalized vinyl monomer such as hydroxyethyl acrylate (HEA) and a soft segment polyol. One embodiment of such a polymer may be made as follows: an equimolar amount of HEA is added dropwise to TDI or IPDI under an inert atmosphere such as nitrogen. The temperature must be kept low (less than 45° C.) so that the vinyl functionality does not polymerize. After the temperature of the mixture has dropped, a stoichiometric amount of a polyol, e.g., difunctional ethylene oxide based diol, is added with a stanous octate catalyst and the mixture heated to 70° C. typically for about 2 hours.

Cross-linking of the polymer may be achieved through a photoinitiated reaction. The photoinitiator may be a 1:1 to mixture of 2,2'-diethoxyacetophenon and N-methyldiethanolamine. An effective amount of photoinitiator is from about 0.3 to about 1.2 weight percent or more particularly about 0.67 weight percent of the mixture added to the urethane acrylates. The cross-linkers which may be used are N-vinylpyrrolidone and polyethyleglycol 200 diacrylate.

The composition of the cross-linkable urethane acrylate systems can be varied in different ways. The molecular weight of the soft segment polyol can be varied while holding the cross-linker content constant. In an alternative approach the cross-linker content can be varied while holding the soft segment content constant. A tri-functional polyol, if used in this reaction, will result in the production of a thermoset foam. The acrylate functionality may also be adjusted in order to vary the degree of cross-linking.

The mixture of urethane acrylate pre-polymer, photoinitiator and crosslinker can be irradiated under an inert atmosphere with a high energy beam after extrusion. The high energy irradiation beam source could be a bank of mercury ultraviolet (UV) lamps or an electron beam (e-beam) source. This high energy beam treatment results in irreversible cross-linking of the polymer to improve web integrity and hold the structure together.

The mixture may be processed by extrusion from a die in the shape of a film, foam, fibrous foam, fiber, and the like. In foam form, a layer of such a polymer absorbs liquid not only because it is made from a superabsorbent but also because it contains many voids typical of foams and these voids provide areas for the storage of liquid.

Particles, fibers, etc., may be added to the extruded polymer as it is produced. In this manner, additives like superabsorbents, wetting agents, colorants, anti-bacterial or anti-viral agents, medicaments or other desired treatments, may be added to the layer.

Figures 2, 3:
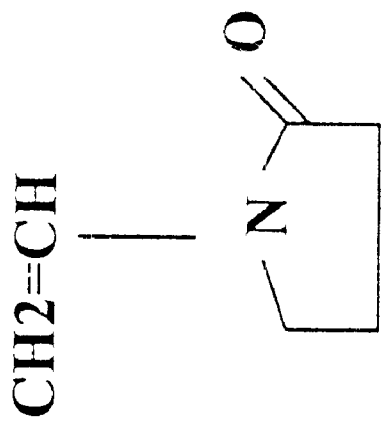

An example of a scheme that describes the synthesis of a urethane formulation is illustrated in FIG. 1. The structure of a polyethylene glycol and N-vinyl pyrollidone photoinitiators are given in FIGS. 2 and 3 respectively.

It should be noted that reactants other than urethanes may be used in the practice of this invention provided the product meets the invention requirements. Reactive moieties such as esters, ethers, amides and the like may be suitable as well.

Another embodiment of this invention is a mixture of toluene di-isocyanate, polyether or polyester polyol, water, and/or various foaming agents and catalysts. The water reacts with isocyanate to produce carbon dioxide that in turn produces the foam structure during the reaction of amine or hydroxy terminated polyetherpolyals, water and other di- or multi-functional low molecular weight cross-linking molecules.

A suitable toluene di-isocyanate is a mixture of 80 percent toluene-2,4 and 20 percent toluene-2,6 di-isocyanates available from the Dow Chemical Company of Michigan under the tradename VORANATE®. The polyol may be polyethylene oxide and the foam stabilizing agents may be silicone based. The reactants generally include an amine catalyst and a stannous octoate catalyst. Materials produced from these reagents may cross-link as they are produced instead of needing additional high energy beam treatment. If made in the form of a foam, for example, this material could be cut in the shape needed for the personal care product and used accordingly. Other additives such as superabsorbents or materials with some functionality can be added to this formulation and foamed in-situ.

In yet another embodiment of this invention, the reactants of the two other embodiments may be combined in a single step to produce a non-cross-linked material with a cellular structure by choosing component reagents of appropriate functionality that can be subjected to a high energy beam to trigger cross-linking. This provides a means of making a superabsorbent material like a thermoplastic and then cross-linking it via the double bond functionality when desired to achieve dimensional stability. The reactants include HEA, a polyether polyol, and isocyanate. A photoinitiator and cross-linker may be included so that the reaction products maybe cross-linked by high energy beam treatment after the production or the fibers or film that has a foam structure.

Polyethylene oxide tends to be crystalline and rigid at room temperature. Upon contact with water or other fluids, however, it becomes amorphous and elastic and remains so because the superabsorbent is cross-linked. The degree of crystallinity and rigidity can be altered by various factors such as molecular weight and whether a co-monomer is present. All of these materials that contain a polyethylene oxide soft backbone thus have triggerable elasticity and the elasticity can be triggered by contact by body fluids and/or by temperature effects such as those generated by the wearer of a personal care product.

In another aspect of this invention, the reactants can be modified in order to make a more elastic product and one which has triggerable elasticity. This may be done, for example, if polyethylene oxide is the polyol chosen for the reaction. Polyethylene oxide is a relatively rigid molecule but is needed as a reactant for absorbency functionality. Polypropylene oxide is a less rigid and more elastic molecule. Some of the polyethylene oxide may be replaced with polypropylene oxide in the reaction in order to increase the flexibility of an otherwise rigid ethylene oxide backbone until its elasticity is triggered by an influence such as, for example, body temperature and/or fluid contact. This triggerable elasticity, due to the contact of the ethylene oxide portion with liquid or due to body temperature, is quite advantageous in terms of comfort and fit of a personal care product.

The polymers of the invention, if in fibrous form, may be mixed with other fibers in, for example, a coforming process or bonding and carding, and air-laying processes, described above. Other processes, such as that disclosed in U.S. Pat. No. 4,902,559 to Eschwey et al. may be used as well. Eschwey teaches a method of mixing fibers and (superabsorbent) particles with filaments as they are produced by mixing them in the downwardly extending air stream, in about the bottom third of the distance between the spinneret and the support onto which the fibers are produced.

Personal care articles usually have multiple layers of material of some sort to absorb liquids from the body. After going through these upper layers, the liquid enters the absorbent portion of the product. The absorbent polymers of this invention may be used to produce a fibrous absorbent core without the traditional addition of particulate superabsorbent. Particulate superabsorbent sometimes escapes from the product, causing a nuisance. Superabsorbent that has migrated within the product is also undesirable as swelling of the particles occurs where it is not necessarily wanted. The superabsorbent of this invention may be easily processed and converted into personal care products like diapers and training pants and due to the dimensional stability, cannot escape from or migrate within the product. If the polymer of this invention is in the form of a foam and additional superabsorbent is added in, for example, particulate form, as described above, escape and migration are impeded because the particles will be held in the interstices and voids within the foam.

The absorbent core is usually placed in a personal care product in an area separated from a wearer by a number of layers. These layers are designed in varying degrees take liquid in and transfer it down to the absorbent so as to stop liquid from re-wetting the skin and from escaping from the product, as well as to keep superabsorbent particles from moving. Many of these layers are fibrous. A superabsorbent from which particles cannot escape is quite attractive as it may contain other functionalities in addition to its absorbent ability. A layer of the polymer of this invention in fibrous form, for example, alone or mixed with other fibers such as pulp and binder fibers, may be able to replace not only the absorbent core but a number of the overlaying layers as well. Such a simplification of the manufacturing process could result in a more efficient usage of energy and resources and result in lower product prices for consumers. As importantly, such a simplified product would be, no doubt, thinner and more comfortable for the wearer. The inventors have provided, therefore, a superabsorbent layer that will have good elastic properties and provide absorbent properties in many forms, is easier to convert into a finished product and is more efficient.

As will be appreciated by those skilled in the art, changes and variations to the invention are considered to be within the ability of those skilled in the art. Examples of such changes and variations are contained in the patents identified above, each of which is incorporated herein by reference in its entirety to the extent consistent with this specification. Such changes and variations are intended by the inventors to be within the scope of the invention.

What is claimed is:

1. A layer for personal care products comprising a superabsorbent acrylate-containing elastic polymer, which polymer is extruded and is dimensionally stable via an irreversible crosslinking reaction, and wherein such polymer comprises the product of a di or multi-functional hydroxy or amine terminated polyether or polyester polyol, coupled through isocyanates.

2. The layer of claim 1 wherein said elastic polymer is extruded in a form selected from the group consisting of fiber, film, foam, fibrous film and fibrous foam.

3. The layer of claim 2 wherein said form is fiber.

4. The layer of claim 1 wherein said polymer is made by reacting an amine or hydroxy terminated polyether polyol with water and an isocyanate.

5. The layer of claim 1 wherein said polymer is made from an acrylate and an isocyanate.

6. The layer of claim 5 wherein said isocyanate is selected from the group consisting of isophorone di-isocyanate and toluene di-isocyanate.

7. The layer of claim 1 wherein said dimensional stabilization is achieved by cross-linking by the use of a high energy beam.

8. The layer of claim 7 wherein said high energy beam is selected from the group consisting of electron beams and ultra-violet beams.

9. The layer of claim 1 further comprising additives selected from the group consisting of pulp, synthetic fibers, particles and mixtures thereof.

10. A diaper comprising the layer of claim 1.

11. A training pant comprising the fibrous layer of claim 1.

12. An incontinence product comprising the fibrous layer of claim 1.

13. A bandage comprising the fibrous layer of claim 1.

14. A sanitary napkin comprising the fibrous layer of claim 1.

* * * * *